US00PP36503P2

(12) United States Plant Patent
Kievit

(10) Patent No.: US PP36,503 P2
(45) Date of Patent: Feb. 25, 2025

(54) ***PHLOX* PLANT NAMED 'Balsashink'**

(50) Latin Name: ***Phlox hybrida (Phlox subulata* X *Phlox stolonifera)***
Varietal Denomination: Balsashink

(71) Applicant: Ball Horticultural Company, West Chicago, IL (US)

(72) Inventor: Christa Kievit, Hem (NL)

(73) Assignee: BALL HORTICULTURAL COMPANY, West Chicago, IL (US)

( * ) Notice: Subject to any disclaimer, the term of this patent is extended or adjusted under 35 U.S.C. 154(b) by 0 days.

(21) Appl. No.: 18/911,976

(22) Filed: Oct. 10, 2024

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 6/70; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phlox* plant named 'Balsashink', characterized by its upright to outwardly spreading and low mounding plant habit; moderately vigorous growth habit; dark green-colored leaves; freely flowering habit; relatively long flowering period; light reddish purple-colored flowers; and good container and garden performance.

2 Drawing Sheets

Figure 1:
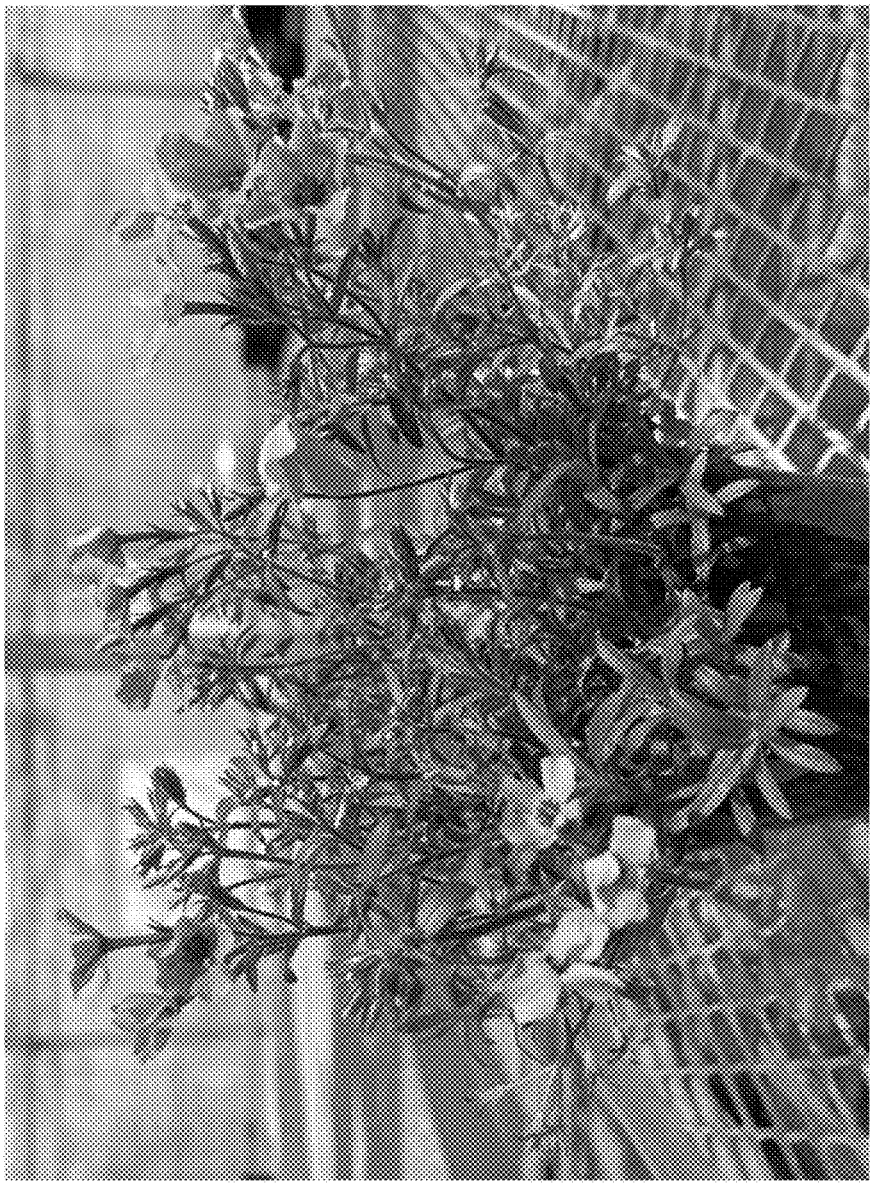

Botanical designation: *Phlox hybrida* (*Phlox subulata* X *Phlox stolonifera*).

Cultivar denomination: 'BALSASHINK'.

BACKGROUND OF THE INVENTION

The present invention relates to a new and distinct cultivar of *Phlox* plant, commonly referred to as Woodland *Phlox*, botanically known as *Phlox hybrida* and hereinafter referred to by the name 'Balsashink'.

The new *Phlox* plant is a product of a planned breeding program conducted by the Inventor in Hem, The Netherlands. The objective of the breeding program was to create new *Phlox* plants with a low mounding to spreading growth habit, numerous flowers and a long flowering time.

The new *Phlox* plant originated from a cross-pollination made by the Inventor in May 2016 in Hem, The Netherlands, of *Phlox subulata* 'Amazing Grace', not patented, as the female, or seed, parent with *Phlox stolonifera* 'Home Fries', not patented, as the male, or pollen, parent. The new *Phlox* plant was discovered and selected by the Inventor as a single flowering plant from within the progeny of the stated cross-pollination in a controlled environment in Hem, The Netherlands in July 2017.

Asexual reproduction of the new *Phlox* plant by vegetative cuttings in a controlled environment in Hem, The Netherlands and West Chicago, Illinois since July 2017 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Balsashink'. These characteristics in combination distinguish 'Balsashink' as a new and distinct *Phlox* plant:

1. Upright to outwardly spreading and low mounding plant habit.
2. Moderately vigorous growth habit.
3. Dark green-colored leaves.
4. Freely flowering habit.
5. Relatively long flowering period.
6. Light reddish purple-colored flowers.
7. Good container and garden performance.

Plants of the new *Phlox* differ primarily from plants of the female parent, 'Amazing Grace', in flower color as plants of the new *Phlox* have light reddish purple-colored flowers whereas plants of 'Amazing Grace' have white-colored flowers with red purple-colored centers. In addition, plants of the new *Phlox* are more mounding than plants of 'Amazing Grace'.

Plants of the new *Phlox* differ primarily from plants of the male parent, 'Home Fries', in flower color as plants of the new *Phlox* have light reddish purple-colored flowers whereas plants of 'Home Fries' have pink-colored flowers. In addition, plants of the new *Phlox* are not as vigorous as plants of 'Home Fries'.

Plants of the new *Phlox* can also be compared to plants of *Phlox subulata* 'Emerald Pink', not patented. In side-by-side comparisons, plants of the new *Phlox* and 'Emerald Pink' differ in the following characteristics:

1. Plants of the new *Phlox* are more uniformly mounding than plants of 'Emerald Pink'.
2. Plants of the new *Phlox* and 'Emerald Pink' differ in flower color as plants of the new *Phlox* have light reddish purple- colored flowers whereas plants of 'Emerald Pink' have pink-colored flowers.

3. Plants of the new *Phlox* flower for a longer period of time than plants of 'Emerald Pink'.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet (FIG. 1) is a side perspective view of typical flowering plant of 'Balsashink' grown in a container.

Figure 2:
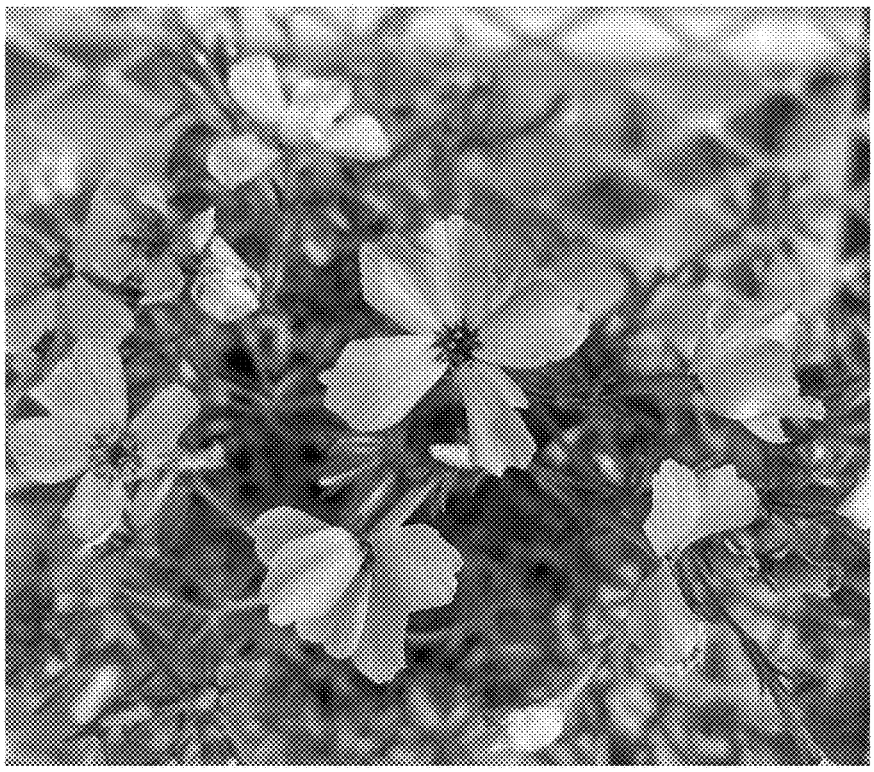

The photograph on the second sheet (FIG. 2) is a close-up view of a typical flowering plant of 'Balsashink'.

DETAILED BOTANICAL DESCRIPTION

The aforementioned photographs and following observations, measurements and values describe plants grown during the late winter and early spring in 10-cm containers in a polyethylene-covered greenhouse in Elburn, Illinois and under cultural practices typical of commercial *Phlox* production. Plants were three months old from planting rooted young plants when the photographs and the description were taken. In the following description, color references are made to The Royal Horticultural Society Colour Chart, Fifth Edition, except where general terms of ordinary dictionary significance are used.

Botanical classification: *Phlox hybrida* (*Phlox subulata* X *Phlox stolonifera*) 'Balsashink'.

Parentage:

*Female, or seed, parent.*—*Phlox subulata* 'Amazing Grace', not patented.

*Male, or pollen, parent.*—*Phlox stolonifera* 'Home Fries', not patented.

Propagation:

*Type.*—By vegetative terminal stem cuttings.

*Time to initiate roots.*—About ten to twelve days.

*Time to produce a rooted young plant.*—About six to seven weeks.

*Root description.*—Medium in thickness, fibrous; typically white to light yellow in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Herbaceous perennial typically grown as a container and garden plant; upright to outwardly spreading and low mounding plant habit; moderately vigorous growth habit.

*Plant height.*—About 14 cm to 15 cm.

*Plant width* (*spread*).—About 28 cm to 30 cm.

*Lateral branches.*—Branching habit: Freely branching habit with numerous primary lateral branches each with potentially two lateral branches developing at every node; pinching enhances branching potential. Length: About 15 cm to 17 cm. Diameter: About 2 mm. Internode length: About 1.5 cm to 1.8 cm. Strength: Strong, wiry and flexible. Aspect: Erect to about 75° from vertical. Texture and luster: Pubescent; moderately glossy. Color, developing: Close to 144A. Color, developed: Close to 146A.

Leaf description:

*Arrangement.*—Opposite, simple; sessile.

*Length.*—About 2.2 cm.

*Width.*—About 5 mm.

*Shape.*—Linear with lanceolate tendencies.

*Apex.*—Acute.

*Base.*—Cuneate.

*Margin.*—Entire, ciliate.

*Texture and luster, upper and lower surface.*—Smooth, glabrous; glossy.

*Venation pattern.*—Single midvein discernible.

*Color.*—Developing leaves, upper surface: Close to 147A. Developing leaves, lower surface: Close to 146A. Fully expanded leaves, upper surface: Close to 147A; midvein, close to 146A. Fully expanded leaves, lower surface: Close to 146A; midvein, close to 146A.

Flower description:

*Flower type and flowering habit.*—Single rotate and salverform flowers arranged in terminal and lateral panicles; flowers face mostly upright to outwardly depending on position on inflorescence; freely flowering habit with about eight to twelve flowers per inflorescence and numerous flowers developing per plant during the flowering season.

*Fragrance.*—Faintly fragrant, sweet and pleasant.

*Natural flowering season.*—Relatively long flowering period; plants flower continuously from early to mid-spring in the garden in northern Illinois; flowers not persistent.

*Flower buds.*—Height: About 6 mm to 7 mm. Diameter: About 3 mm to 4 mm. Shape: Narrowly ovate. Texture and luster: Smooth, glabrous; slightly glossy. Color: Close to 146A.

*Inflorescence height.*—About 5.5 cm.

*Inflorescence diameter.*—About 5.5 cm.

*Flower diameter.*—About 2.3 cm.

*Flower depth.*—About 2 cm.

*Flower throat diameter.*—About 1 mm to 2 mm.

*Flower tube length.*—About 1.6 cm.

*Flower throat diameter.*—About 2 mm.

*Petals.*—Quantity per flower: Typically five in a single whorl; petals fused at the base into a narrow tube. Lobe length: About 1.1 cm. Lobe width: About 7 mm to 8 mm. Lobe shape: Obcordate. Lobe apex: Cordate. Lobe margin: Entire; slightly undulate. Lobe texture and luster, upper and lower surfaces: Smooth, glabrous; matte. Throat texture and luster: Smooth, glabrous; matte. Tube texture and luster: Pubescent; matte. Color: When opening, upper surface: Close to N75A. When opening, lower surface: Close to 76A. Fully opened, upper surface: Close to N75A; venation, close to N75A; nectar guides, streaks or spots, close to 83A; color becoming closer to N75B with subsequent development. Fully opened, lower surface: Close to 76A; venation, close to 76A; color becoming closer to 76B with subsequent development. Throat: Close to 76B to 76C; venation, close to 76B to 76C. Tube: Close to 76B; venation, close to 76B.

*Sepals.*—Quantity per flower: Typically five in a single whorl, fused towards the base; calyx, tubular in shape. Length: About 9 mm. Width: About 1.5 mm. Shape: Linear. Apex: Acuminate. Margin: Entire. Texture and luster, upper and lower surfaces: Pubescence; moderately glossy. Color: When opening and fully opened, upper surface: Close to 146A. When opening and fully opened, lower surface: Close to between 144A and 146A.

*Peduncles*.—Length: About 2.4 cm. Diameter: Less than 1 mm. Strength: Moderately strong, wiry and flexible. Aspect: Mostly erect to about 45° from lateral branch axis. Texture and luster: Pubescent; moderately glossy. Color: Close to 144A.

*Pedicels*.—Length: About 8 mm to 12 mm. Diameter: Less than 1 mm. Strength: Moderately strong, wiry and flexible. Aspect: Erect to about 40° to 45° from peduncle axis. Texture and luster: Pubescent; moderately glossy. Color: Close to 144A.

*Reproductive organs*.—Stamens: Quantity per flower: Typically five; adnate to the throat. Filament length: About 1.3 cm. Filament color: Close to 76C to 76D. Anther size: About 0.25 mm by 1 mm. Anther shape: Oblong. Anther color: Close to 17A. Pollen amount: Moderate to abundant. Pollen color: Close to 17A. Pistils: Quantity per flower: One. Pistil length: About 1.7 cm. Stigma diameter: About 2 mm. Stigma shape: Cleft, three-parted. Stigma color: Close to N144A to N144B. Style length: About 1.4 cm. Style color: Close to 145B to 145C. Ovary color: Close to 144A.

*Seeds and fruits*.—To date, seed and fruit development have not been observed on plants of the new *Phlox*.

Garden performance: Plants of the new *Phlox* have been observed to have good garden performance and to tolerate rain, wind, temperatures ranging from about −32° C. to about 35° C. and to be suitable for USDA Hardiness Zones 4a to 8b.

Pathogen & pest resistance: Plants of the new *Phlox* have shown relative resistance to Powdery Mildew (Erysiphaceae family). To date, plants of the new *Phlox* have not been observed to be resistant to pests and other pathogens common to *Phlox* plants.

It is claimed:

1. A new and distinct *Phlox* plant named 'Balsashink' as herein illustrated and described.

* * * * *